United States Patent [19]

Navia et al.

[11] Patent Number: 5,298,611

[45] Date of Patent: Mar. 29, 1994

[54] SUCRALOSE PENTAESTER PRODUCTION

[75] Inventors: Juan L. Navia, Athens; Robert E. Walkup, Watkinsville, both of Ga.; Nicholas M. Vernon, Durham, England; Robert E. Wingard, Jr., Athens, Ga.

[73] Assignee: McNeil-PPC, Inc., Milltown, N.J.

[21] Appl. No.: 30,518

[22] Filed: Mar. 12, 1993

[51] Int. Cl.$^5$ .................. C07H 13/04; C07H 13/06; C07H 13/08

[52] U.S. Cl. .................. 536/4.1; 536/115; 536/123.13; 536/125; 127/30; 127/42; 127/46.1; 127/47; 127/58

[58] Field of Search .......... 536/4.1, 115, 125, 123.13; 127/30, 42, 46.1, 47, 58

[56] References Cited

U.S. PATENT DOCUMENTS

| | | | |
|---|---|---|---|
| 4,380,476 | 4/1983 | Mufti et al. | 127/46.3 |
| 4,612,373 | 9/1986 | Khan et al. | 536/120 |
| 4,950,746 | 8/1990 | Navia | 536/119 |
| 4,980,463 | 12/1990 | Walkup et al. | 536/124 |
| 5,023,329 | 6/1991 | Neiditc et al. | 536/119 |
| 5,089,608 | 2/1992 | Walkup et al. | 536/124 |

FOREIGN PATENT DOCUMENTS 0475619  3/1992  European Pat. Off. .

*Primary Examiner*—Nathan M. Nutter
*Attorney, Agent, or Firm*—Charles J. Metz

[57] ABSTRACT

A process for producing substantially pure sucralose pentaester from a mixture of 6-O-acyl-4,1',6'-trichloro-4,1',6'-trideoxygalactosucrose in a reaction medium comprising a tertiary amide, wherein said process comprises the steps of:

(a) recovering the 6-O-acyl-4,1',6'-trichloro-4,1',6'-trideoxygalactosucrose from said mixture;

(b) peracylating the 6-O-acyl-4,1',6'-trichloro-4,1',6'-trideoxygalactosucrose product of step (a) to produce thereby 4,1',6'-trichloro-4,1',6'-trideoxygalactosucrose pentaester; and (c) crystallizing the 4,1',6'-trichloro-4,1',6'-trideoxygalactosucrose pentaester product of step (b) to produce substantially pure 4,1',6'-trichloro-4,1',6'-trideoxygalactosucrose pentaester.

17 Claims, 2 Drawing Sheets

SUCRALOSE PENTAESTER PRODUCTION

The invention relates to a process for the production of sucralose pentaester.

BACKGROUND OF THE INVENTION

The artificial sweetener 4,1',6'-trichloro-4,1',6'-trideoxyoalactosucrose ("sucralose") is derived from sucrose by replacing the hydroxyls in the 4, 1', and 6' positions with chlorine. (In the process of making the sweetener, the stereo configuration at the 4 position is reversed - hence the compound is a qalactosucrose.) The direction of the chlorine atoms to only the desired positions is a major synthesis problem because the hydroxyls that are replaced are of differing reactivity; two are primary and one is secondary. The synthesis is further complicated by the fact that the primary hydroxyl in the 6 position is unsubstituted in the final product.

A number of different synthesis routes for the preparation of sucralose have been developed in which the reactive hydroxyl in the 6 position is first blocked, as by an ester group, prior to the chlorination of the hydroxyls in the 4, 1', and 6' positions, followed by hydrolysis to remove the ester substituent to produce sucralose. Several of such synthesis routes involve tin-mediated syntheses of sucrose-6-esters. Illustrative are the tin-mediated routes disclosed by Navia (U.S. Pat. No. 4,950,746), Neiditch et al. (U.S. Pat. No. 5,023,329), Wingard et al. (U.S. patent application Ser. No. 870,190, filed Apr. 13, 1992—published, as EP-A-0 475 619 A1), and Walkup et al. (U.S. Pat. No. 5,089,608 - Walkup et al.-I).

The above-illustrated tin-mediated syntheses have in common the preparation of a sucrose-6-ester that can be chlorinated to produce a sucralose-6-ester (that is, sucralose having an ester group substituent at the 6 position). The sucrose-6-ester can be chlorinated by the process described in Walkup et al., U.S. Pat. No. 4,980,463 (Walkup et al.-II). The Walkup et al.-II process produces as a product of the chlorination a mixture of 6-O-acyl-4,1',6'-trichloro-4,1',6'-trideoxyoalactosucrose ("sucralose-6-ester") in a tertiary amide solvent such as N,N-dimethylformamide. The chlorination reaction product mixture also contains water, salts, and chlorinated carbohydrate byproducts.

The present invention provides an improved method for producing sucralose from a mixture of 6-O-acyl-4,1',6'-trichloro-4,1',6'-trideoxyoalactosucrose in a tertiary amide solvent such as N,N-(dimethylformamide.

BRIEF SUMMARY OF THE INVENTION

The invention provides a process for producing substantially pure 4,1',6'-trichloro-4,1',6'-trideoxyqalactosucrose pentaester from a reaction mixture comprising 6-O-acyl-4,1',6'-trichloro-4,1',6'-trideoxyoalactosucrose and a tertiary amide such as N,N-dimethylformamide, wherein said process comprises the steps of:

(a) recovering the 6-O-acyl-4,1',6'-trichloro-4,1',6'-trideoxygalactosucrose from said mixture;

(b) peracylating the 6-O-acyl-4,1',6'-trichloro-4,1',6'-trideoxygalactosucrose product of step (a) to produce thereby 4,1',6'-trichloro-4,1',6'-trideoxygalactosucrose pentaester; and (c) crystallizing the 4,1',6'-trichloro-4,1',6'-trideoxyoalactosucrose pentaester product of step (b) to produce substantially pure 4,1',6'-trichloro-4,1',6'-trideoxygalactosucrose pentaester.

The product of step (c) can then be de-acylated to produce sucralose in high yield and purity.

DETAILED DESCRIPTION OF THE INVENTION

Nomenclature and Abbreviations

Figure 1:
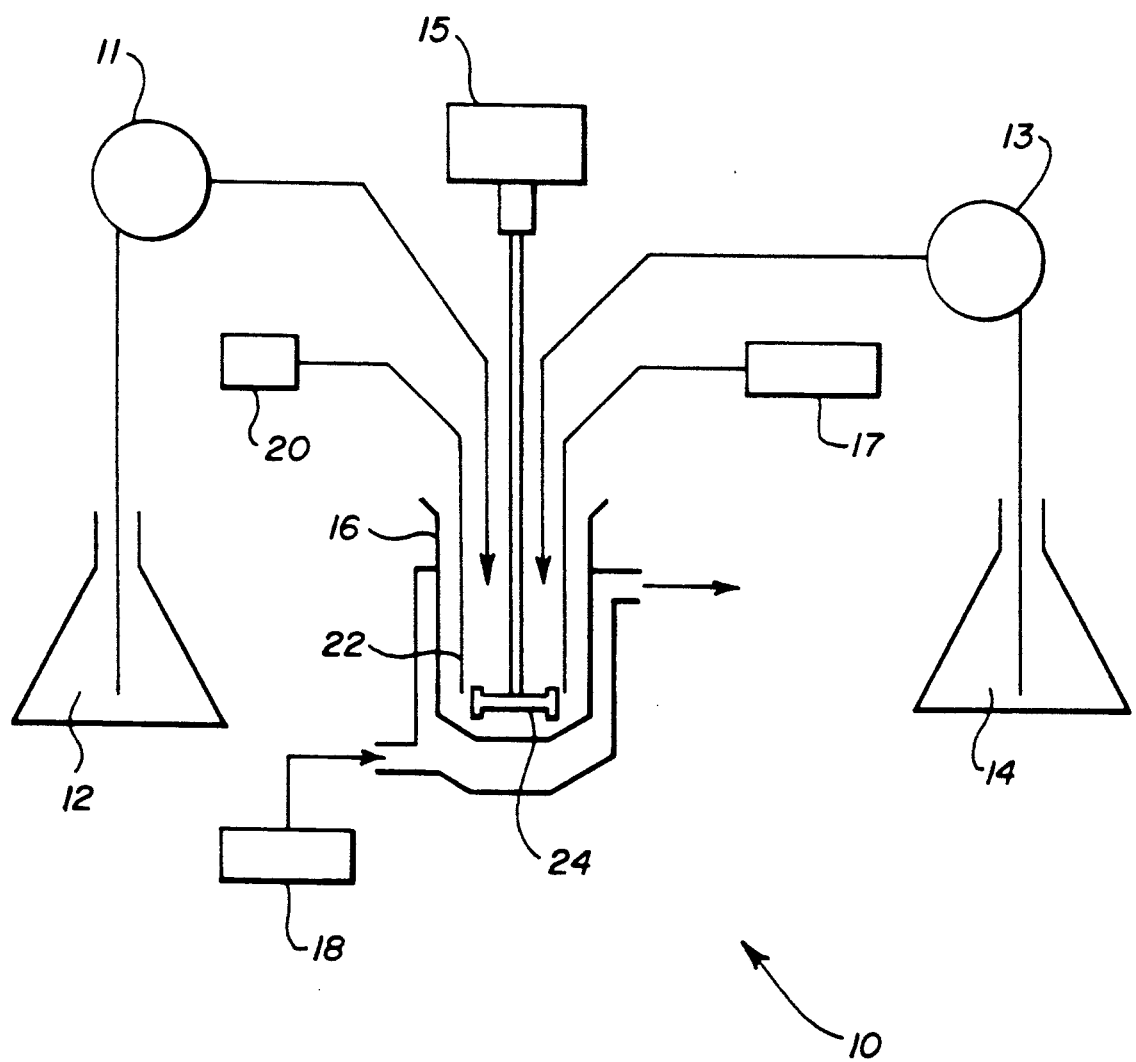
FIG. 1 is a diagram of a laboratory-scale dual-stream quench apparatus designed for neutralizing the acid present in sucralose-6-ester chlorination product reaction mixtures.

As used in this application, the following short names and abbreviations have the indicated meaning:

Sucralose=4,1',6'-trichloro-4,1',6'-trideoxygalactosucrose;
DMF=N,N-dimethylformamide;
S-6-A or sucrose-6-acetate[1]=6-O-acetylsucrose;
S-6-B or sucrose-6-benzoate=6-O-benzoylsucrose;
Sucralose-6-acetate or 4,1',6'-trichloro-4,1',6'-trideoxygalactosucrose-6-acetate=4,1',6'-trichloro-4,1',6'-trideoxygalactosucrose-6-acetate;
Sucralose-6-benzoate or 4,1',6'-trichloro-4,1',6'-trideoxygalactosucros-6-benzoate=4,1',6'-trichloro-4,1',6'-trideoxygalactosucrose-6-benzoate; and
Sucralose pentaacetate=4,1',6'-trichloro-4,1',6'-trideoxygalactosucrose pentaacetate.

The process of the invention employs as its starting reaction mixture a composition comprising 6-O-acyl-4,1',6'-trichloro-1',6'-trideoxygalactosucrose in a tertiary amide (preferably DMF) reaction medium, such as the neutralized (quenched) product of the chlorination reaction described by Walkup et al.-II, cited above.

On the laboratory scale, the crude chlorination product may be quenched in a batch operation by the addition (in one portion) of one molar equivalent (basis phosgene) of ice-cold aqueous solutions or slurries of the alkali or alkaline earth metal hydroxides following the teachings of Walkup et al.-II. Preferred alkaline agents include the hydroxides of sodium, potassium, and calcium. More dilute aqueous alkaline solutions, such as for example 4 to 8N sodium hydroxide, are preferred.

In a preferred method of practice of this quench method, cold aqueous alkali is added with vigorous stirring as rapidly as possible in a quantity sufficient to raise the pH to 8–10. After stirring several minutes at this mildly elevated pH, the quenched solution is neutralized to pH 5–7 by the addition of an acid, such as, for example, concentrated aqueous hydrochloric acid or glacial acetic acid. The brief treatment of the quenched chlorination reaction mixture at pH 8–10 has the beneficial effect of insuring that all of the hydroxyl groups that have not been replaced by chlorine atoms are returned to their original hydroxyl group form (i.e., they are deprotected).

The batch method for quenching the crude chlorination product mixture suffers from scale limitations owing to inefficiencies in heat and mass transport. An improved method, known as the "dual-stream" or "concurrent addition" method, involves mixing streams of aqueous alkali and cooled (to about room temperature) crude chlorination product together at carefully metered rates with vigorous agitation under conditions of pH and temperature control. The primary advantages of the dual-stream quench method are that it provides for complete control of pH, temperature, and rate of mixing throughout the course of the quench. Thus, side reactions resulting in product losses are minimized. A further advantage of the dual-stream quench method is that it may be operated continuously by using a quench vessel fitted with either a bottom drain or a pump. By operating the dual-stream quench method in a continuous mode, a relatively large amount of crude chlorination product can be processed using a quench vessel of modest size. This continuous operation is a rough approximation of an inline mixing process that might be employed for quenching in a commercial operation.

The laboratory-scale dual-stream quench apparatus consists of a temperature-compensated pH control pump for the addition of aqueous alkali, a second pump for the constant addition of the crude chlorination product mixture, a quench vessel fitted with an external jacket to allow for the flow of coolant, a thermostated chiller to both cool and pump the coolant, and various pieces of auxiliary equipment such as a mechanical stirrer, thermocouples, etc. The apparatus is operated by adding the crude chlorination product mixture to the vessel at a constant rate. The pH control pump is fitted with a pH meter and a pH probe which is placed in the quench vessel. The control pump adds aqueous caustic automatically in response to programmed instructions for maintaining the pH of the mixture at a certain value. Vigorous agitation of the solution in the quench vessel is required. Experiments have indicated that inadequate mixing will result in domains of inadequate pH control within the quench mixture, resulting in the loss of product to side reactions.

Using a 1500-ml jacketed quench vessel, it was determined that crude sucralose-6-ester product mixtures could be quenched efficiently using a chlorination mixture constant feed rate of about 10 ml per minute, a quench mixture temperature of about 15° C. (coolant temperature 5° C.), a four-bladed propeller-type stirrer with a stirring rate sufficient to insure good mixing, and a pH control setting of pH 8.5 on the pH control pump. These results were obtained with 3N or 4N NaOH as the alkaline agent, and with a starting charge of about 100 ml of between 3:1 to 1:3 DMF-H$_2$O in the quench vessel (in order to have sufficient solution volume for accurate pH measurement during the early stages of the quench). A diagram of a laboratory-scale dual-stream quench apparatus is shown in FIG. 1.

DMF Removal

Following the quench, sucralose-6-ester is recovered from a mixture containing DMF, water, salts, and chlorinated carbohydrate byproducts. The salts are approximately 1:1 sodium chloride:dimethylamine hydrochloride, but small amounts of sodium formate also appear to be present. The direct extraction of sucralose-6-ester from the quenched product mixture is complicated by the presence of DMF and its propensity to distribute between both phases. Laboratory experimentation established that DMF can be removed from the quenched chlorination product mixture by steam distillation without any detectable decomposition of the desired chlorination product. The DMF can subsequently be recovered from the aqueous overheads by distillation, and can then be recycled.

Figure 2:
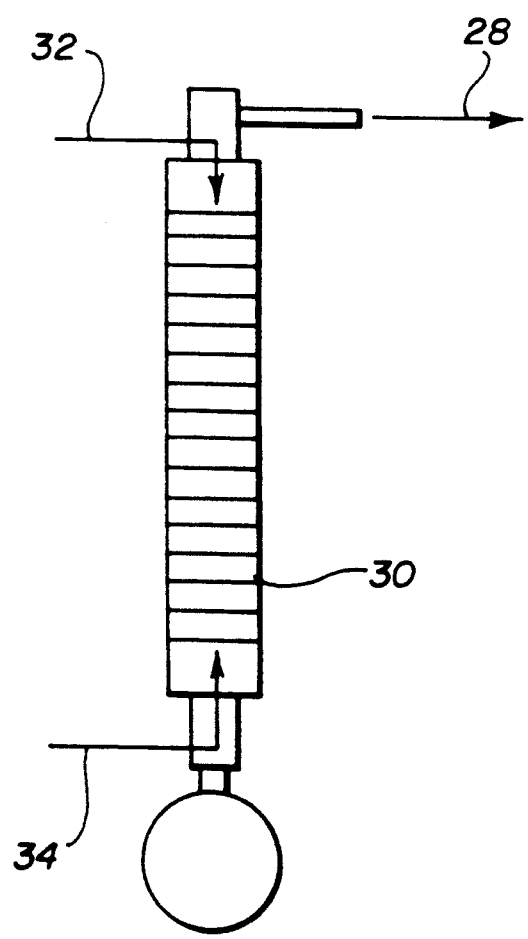
FIG. 2 is a diagram of a laboratory-scale falling-film packed-column steam distillation apparatus designed for stripping the DMF from quenched sucralose-6-ester chlorination product reaction mixtures.

An example of a laboratory-scale falling-film packed-column steam distillation apparatus designed for stripping the DMF from quenched sucralose-6-ester chlorination products is shown in FIG. 2. The stripping column is a 5.0-cm diameter, 90-cm long vacuum-jacketed distillation column packed with 5-mm Raschig rings or other suitable packing. Alternatively, a 15-plate, jacketed, Oldershaw column has been used. The quenched product, which is typically preheated, is introduced into the top of the column at a rate of about 5.0-5.5 grams per minute. Steam is introduced into the column through a sidearm located at the bottom of the column. As condensate-free steam is required, the steam is past through a "preboiler" to trap any condensate carried over. In the laboratory, this preboiler is typically a small multineck flask fitted with a heating mantle. Typical steam feed rates are in the range of 38-47 grams per minute (calculated by adding the weights of overhead and bottom products, and then subtracting the weight of chlorination feed), which corresponds to a steam-to-feed ratio ranging from 4:1 to 12:1, with steam to feed ratios of between 7.5:1 and 9:1 being typical for the packed column assembly. The preferred embodiment would use more plates with a lower steam:feed ratio, e.g., 15 plates with a steam/feed ratio of about 4:1.

The preheating of the quenched chlorination feed before it is introduced onto the top of the column is conducted in order to increase the efficiency of the stripping operation. Preheating is typically conducted in the laboratory by passing the feed through an enclosed glass coil apparatus heated with a secondary source of steam. The feed is normally heated to about 90°-95° C. The efficiency of DMF removal can also be enhanced by employing a "reboiler" (i.e., by heating the bottoms product in such a way that it refluxes up into the stripping column).

Temperatures are advantageously measured at two places on the apparatus using thermocouple devices. In addition to the quenched chlorination feed temperature described above, the temperature of the vapors passing through the distillation column head are also measured. Head vapor temperatures are typically in the range of from about 99° C. to about 104° C.

A typical quenched chlorination product of sucrose-6-acetate contains about 1.5-5 wt % sucralose-6-ester, about 0.5-1.5 wt % of various other chlorodeoxysucrose derivatives, about 35-45 wt % DMF, about 35-45 wt % water, and about 12-18 wt % salts. After passage of such product mixtures through the laboratory-scale steam-stripping apparatus, bottoms products will typically consist of about 1-3 wt % sucralose-6-ester, about 0.3-1.0 wt % of various other chlorodeoxysucrose derivatives, about 0.1-0.5 wt % DMF, about 80-90 wt % water, and about 8-12 wt % salts (expressed as NaCl, based on sodium and chloride assays).

Under typical laboratory conditions (see Example which involve a column residence time of 7-10 minutes, no decomposition of sucralose-6-acetate is detectable, provided the pH of the quenched chlorination feed is neutral to slightly acidic (pH 5.0-7.0).

SUCRALOSE-6-ESTER EXTRACTION

Following the steam strip, sucralose-6-ester may be readily isolated by extraction of the DMF-depleted aqueous brine solution with a variety of organic solvents. These solvents include methyl acetate, ethyl acetate, methyl ethyl ketone, methyl iso-butyl ketone, methyl iso-amyl ketone, methylene chloride, chloroform, diethyl ether, methyl tert-butyl ether, and the like. A preferred solvent, for reasons of extraction selectivity, ease of recycle, and toxicological safety, is ethyl acetate.

Sucralose-6-ester isolation is typically conducted in the laboratory by first partially evaporating the crude steam-stripped product. About half the water present may optionally be removed, producing a solution containing about 2-5 wt % carbohydrates and about 15-25 wt % salts. Isolation is normally conducted by carrying out three sequential extractions with ethyl acetate or other appropriate solvent. The extracts are combined, and may optionally be washed with water (to partially remove DMF and dichlorodideoxysucrose derivatives which to some extent are partitioned into the organic phase). Evaporation of the solvent produces crude solid sucralose-6-ester.

These crude solid products typically contain about 70-80 wt % sucralose-6-ester and about 7-16 wt % of various chlorodeoxysucrose derivatives (both acylated and nonacylated), with varying degrees of chloro-substitution. These crude solids also typically contain small residual amounts of DMF, water, and ethyl acetate. It is desirable to minimize the water content of these crude solids (e.g., by conducting the brine wash of the combined extracts as described above), because the next step of the process involves treating the material with acetic anhydride, which will be partially consumed by the water present. Typical experimental procedures for the extraction and isolation of sucralose-6-ester are provided in Examples 1-3.

SUCRALOSE PERACYLATE OR PENTAESTER PREPARATION AND PURIFICATION

Sucralose-6-ester is exhaustively acylated by treatment with an acylating agent such as acetic anhydride, and the sucralose pentaester thus produced is purified by extractive crystallization. Peracylation is typically conducted by heating the crude solid sucralose-6-ester such as sucrose-6-acetate with a moderate excess of acetylating agent such as acetic anhydride in the presence of an acylation catalyst, such as pyridine, triethylamine, sodium acetate, or other art-known materials. There are a number of nonhydroxylic organic solvents which can be employed as cosolvents, if desired. These include ethyl acetate, methyl ethyl ketone, methylene chloride, methyl tert-butyl ether, toluene, and the like. However, in the case of acetylation, the acetic anhydride is itself a satisfactory solvent for the conversion, thus eliminating the need for a cosolvent in this case.

The amount of excess acetic anhydride employed is minimized for economic reasons. A 25-50 molar % excess (basis all free carbohydrate hydroxyl groups and water present) has been found to be sufficient for reactions conducted in adequately dry media. Reaction temperatures in the 30°-50° C. range are satisfactory for providing complete conversion within several hours, although temperatures of up to the boiling point of acetic anhydride (138° C.) may be employed if a faster rate of conversion is desired.

After the peracylation is complete, the reaction mixture is typically diluted with an appropriate solvent such as toluene (from about 5 to about 10 volumes, relative to weight of isolated sucralose-6-ester; e.g., from 5-10 ml toluene/g sucralose-6-ester starting reactant in the peracylation reaction), cooled to below about 20° C., and treated with water (from about 2 to about 4 volumes, basis isolated sucralose-6-ester). The biphasic mixture is then cooled to below about 5° C., seeded with authentic sucralose pentaester, and agitated until crystallization is complete.

The presence of water in the crystallization medium serves two purposes. The water destroys the residual excess acetic anhydride present, and it also provides a second phase during the crystallization which, in effect, turns the toluene crystallization into an extractive purification. In the extractive crystallization the sucralose pentaester is soluble in the toluene phase, while the polar materials present, such as acetic acid, DMF, and trace amounts of salt, are soluble in the aqueous phase. Since the vast bulk of the impurities present in the product mixture following peracetylation are both extremely polar and water soluble, this biphasic crystallization is effective at producing a high yield of a high quality product.

Toluene may be replaced by other solvents in the above-described purification scheme. These alternate solvents include, but are not limited to, benzene, mixed xylenes, cyclohexane, methyl tert-butyl ether, methyl ethyl ketone, and the like, plus mixtures of these. The primary criteria for this solvent are that it be a suitable recrystallization solvent for sucralose pentaester.

Sucralose pentaester products isolated from toluene-based extractive crystallizations are typically in the range of from about 85 wt % to about 95 wt % pure. The bulk of the remainder of the weight of these products is made up of water and (primarily) toluene.

Contamination of the sucralose pentaester produced by the biphasic crystallization by carbohydrate-based impurities is nominal. It is this high level of carbohydrate purity which makes this sucralose pentaester product suitable for conversion to sucralose. Typically, the carbohydrate-based purity of the sucralose pentaester following the toluene-water crystallization is greater than 98 wt %, most often greater than 99 wt %.

The yields for the isolated crystalline sucralose pentaester 10 afforded at this step of the process are typically from about 90% to about 95% based upon crude solid sucralose-6-ester. Yields based on sucrose-6-ester utilized in the chlorination typically range from about 45% to about 55%. Overall yields from sucrose are normally in the range of from about 30% to about 40%. The Examples provide experimental details for the conversion of crude solid sucralose-6-acetate and crude solid sucralose-6-benzoate into crystalline sucralose pentaester. Example 2 provides an experimental procedure for the conversion of a sample of this sucralose pentaester into sucralose.

Optional Sucralose Pentaester Recrystallization

If sucralose pentaester of higher purity than that produced in the biphasic crystallization is desired, it may be generated by recrystallization. This may be carried out by dissolving the sucralose pentaester in about from 7 to about 10 volumes (basis sucralose pentaester mass) of toluene at from about 80° C. to about 100° C., and then allowing the solution thus produced to cool slowly, with agitation, to room temperature. Recovery is on the order of from about 84% to about 89%.

Solvents other than toluene may be employed for this optional recrystallization. These other recrystallization solvents include benzene, mixed xylenes, methanol, ethanol, ethyl acetate, methyl ethyl ketone, methyl tert-butyl ether, and the like, plus mixtures of these. Example 3 provides experimental details for the recrystallization of a sample of crystallized sucralose pentaester from toluene, followed by the conversion of this additionally purified material into sucralose.

The above-described process has a number of advantages over other art-known processes for the production of sucralose pentaester. Said advantages are especially relevant to the commercial-scale manufacture of this valuable precursor of the nonnutritive sweetener sucralose. One of these advantages is that, for example, S-6-A and S-6-B (which are used to produce the 6-O-acyl-4,1',6'-trichloro-4,1',6'-trideoxygalactosucrose-6-ester starting reactant of the present invention) can be produced contaminated by residual sucrose and undesirable sucrose mono- and diacylates, and can be chlorinated without a requirement for producing isolated and purified solid S-6-A or S-6-B. Crystallization of the sucralose pentaester in accordance with this invention removes the carbohydrate contaminants.

Another of these advantages is that the DMF is readily and essentially completely removed from the product stream by a falling-film packed-column steam distillation operation termed "steam stripping". Efficient removal of DMF is important for two reasons. First, since DMF is a relatively expensive organic solvent, it is important that it be recovered and recycled in a cost-effective manner. The steam-stripping process allows for this to be accomplished. Second, removal of the DMF from the chlorination product stream allows the extraction of sucralose-6-ester to function smoothly and efficiently. If the DMF is not removed prior to the extraction, undesirable partitioning of the various chlorinated carbohydrate products between the aqueous and organic phases is observed.

Additionally, since the sucralose-6-ester can be cleanly and efficiently extracted, crude sucralose-6-ester (i.e., that afforded by the direct evaporation of the extraction solvent) is obtained in high yield (extraction efficiencies are typically 90–95%). Sucralose-6-ester can be crystallized from ethyl acetate at a high state of purity (normally 85–90% pure exclusive of residual organic solvents and moisture, which are not detrimental to the process). This high purity of the crude sucralose-6-ester provides for a high-yield conversion to high-quality sucralose pentaester. The sucralose pentaester generated by this method is normally of sufficient purity that it may be directly used for sucralose production without the need to resort to additional purification (by, for example, recrystallization) prior to deacylation to sucralose (as is the case for other art-known sucralose pentaester production processes). If any purification is desired, one optional recrystallization from, for example, toluene is normally sufficient to produce sucralose pentaester suitable for sucralose production.

The examples below illustrate the invention utilizing sucralose-6-acetate or sucralose-6-benzoate as the sucralose-6-ester in the starting reaction mixture. However, other sucralose-6-esters, such as sucralose-6-propionate, sucralose-6-butanoate, and the like, may be used as the sucralose-6-ester.

The Examples below illustrate the invention.

EXAMPLE 1

Isolation of Solid Sucralose Pentaacetate From a Phosgene Chlorination Product Made From a Sucrose-6-Acetate Syrup 710 Grams of crude aqueous chlorinated mixture prepared by the method of Neiditch et al. was employed as the starting reaction mixture. This reaction mixture, a dark aqueous solution, was determined by HPLC analysis to contain 4.35 wt % sucralose-6-acetate (30.9 g, 70.2 mmol), 0.7 wt % of various other chlorodeoxysucrose derivatives. Additional assays showed that this solution contained about 40 wt % DMF, about 38 wt % water, and about 15 wt % chloride salts (NaCl and dimethylamine hydrochloride), in addition to lesser amounts of sodium formate.

The above-described mixture was steam stripped of DMF using a 5.0-cm diameter, 90-cm length, vacuum-jacketed distillation column packed with 5-mm Raschig rings. A reboiler was not employed. The product mixture (heated to about 105° C.) was introduced into the top of the column at a rate of about 5.0–5.5 grams per min at a steam-to-feed ratio (by wt) of about 7.5–8.5. The distillation overheads were assayed by gas chromatography and found to contain about 5.6 wt % DMF. The distillation bottoms (982 g) were assayed by various techniques and found to contain about 0.2 wt % DMF, about 85 wt % $H_2O$, and about 11 wt % salts (expressed as NaCl). Carbohydrate composition was determined by HPLC analysis to be 3.15 wt % sucralose-6-acetate and 0.11 wt % of other chlorodeoxysucrose derivatives.

The steam-stripped carbohydrate solution was subjected to rotary evaporation (water-aspirator vacuum, 50° C. bath) to reduce its volume to about 500 ml. The solution was transferred to a 1000-ml separatory funnel and extracted with ethyl acetate ($3 \times 250$ ml). The combined extracts were washed with water ($1 \times 100$ ml), saturated aqueous sodium chloride solution ($1 \times 50$ ml), and evaporated (rotary evaporator, water-aspirator vacuum, 40° C. bath) to produce a light-tan solid which was further vacuum dried (25° C./1.0 mm Hg/24 hr) to a weight of 36.7 g. Carbohydrate composition was determined by HPLC analysis to be 76.2 wt sucralose-6-acetate (27.9 g, 63.5 mmol, 90.5% recovery from the crude quenched chlorination product mixture) and 11.5 wt % of various other chlorodeoxysucrose derivatives. Additional assays showed the solid to contain about 1.4 wt % DMF, about 8.4 wt % ethyl acetate, and about 2.4 wt % water.

The crude solid was treated with 65.0 g (637 mmol) of acetic anhydride and a few drops of pyridine at 50° C. with magnetic stirring under argon for 24 hr. Silica-gel TLC ($Et_2O$) was employed to follow the formation of sucralose pentaester ($R_f$ 0.7). The reaction mixture was diluted with 300 ml of toluene, cooled in an ice bath, treated with 100 ml of $H_2O$ in three portions over 30 min, seeded with authentic sucralose pentaester, and then stirred at 5° C. overnight. The resulting crystalline solid was collected on a coarse-frit sintered glass filter, washed with 50 ml of ice-cold toluene, and vacuum dried (45° C./1.0 mm Hg/60 hr). The dried product weighed 40.1 g, and was found to consist of 95.1 wt % sucralose pentaester (38.1 g, 62.7 mmol, 98.7% yield of crude solid sucralose-6-acetate) by HPLC assay.

The overall yield of solid sucralose pentaester from sucrose for this set of experiments was 38.0%. This solid product is suitable for conversion into high-quality sucralose.

EXAMPLE 2

Preparation of Sucralose From Sucralose Pentaacetate Produced by the Method of Example 1

A 52.0 g sample of 88.6% pure sucralose pentaacetate (46.1 g, 75.8 mmol), prepared according to the method of Example 1, was slurried in 500 ml of methanol in a 1000-ml, three-neck, round-bottom flask equipped with mechanical stirrer and argon inlet. The slurry was treated with 20.0 g of 20 wt % sodium methoxide (4.00 g, 74.1 mmol) in methanol, and stirred at room temperature under argon. The reaction mixture was homogeneous after 10 min, and sucralose ($R_f$ 0.5) formation was judged complete by silica-gel TLC (4:1, $CH_2Cl_2$—$CH_3OH$, sprayed with 5% ethanolic $H_2SO_4$ and charred) after 120 min.

The reaction mixture was quenched with acetic acid (5.00 g, 83.3 mmol), evaporated to dryness (rotary evaporator, aspirator vacuum, 30° C. water bath), and then dried at high vacuum (25° C./0.5 mm Hg/18 hr) to remove as much of the methanol, methyl acetate, and excess acetic acid as possible. The solid mixture of sodium acetate and sucralose thus produced (36.6 g) was dissolved in about 40 ml of water at 80° C., and the resulting solution allowed to cool to room temperature with magnetic stirring and seeded with authentic sucralose. After stirring overnight, the product was filtered, washed with a small amount of cold water, and vacuum dried (25° C./0.5 mm Hg/12 hr). The crystalline solid (20.4 g) was shown by HPLC assay to consist of 99.5 wt % sucralose (20.3 g, 51.0 mmol, 67.3% yield) and 0.5 wt % other chlorinated sucrose derivatives.

EXAMPLE 3

Purification of Sucralose Pentaacetate by Optional Toluene Recrystallization and Conversion into Sucralose In order to challenge the ability of the optional toluene crystallization to purify sucralose pentaester, a DMF-based sucrose-6-acetate syrup (prepared according to the method of Navia) was employed as the starting reaction mixture. This syrup was shown by HPLC analysis to contain 40.4 wt % sucrose-6-acetate (285 g, 0.742 mol, 67.4% yield). A combination of further analyses showed the syrup to also contain a 7.1 wt % other acetylated sucrose derivatives, 2.1 wt % unreacted sucrose, 0.1 wt % tin, and 0.1 wt % water, with the remainder being DMF.

The syrup was "doped" with sucrose to a final HPLC assay of 32.3 wt % sucrose-6-acetate, 4.4 wt % other sucrose acetates, and 2.7 wt % sucrose. This syrup was chlorinated according to the method described by Navia, and the resulting chlorination product was peracetylated essentially as described in Example 1, except that the steam-strip (DMF removal) operation was not performed (i.e., the ethyl acetate extractions were conducted with the DMF still present in the chlorination product mixture).

A 2.00 g sample of the crude sucralose pentaacetate thus produced was treated with 5 drops of 20 wt % sodium methoxide in 15 ml of methanol with stirring at room temperature for 120 min. After quenching with 5 drops of glacial acetic acid, the product solution was analyzed by HPLC and found to consist of 93.5% sucralose, 6.4 wt % other chlorinated sucrose derivatives, and 0.4% sucralose-6-acetate, basis total carbohydrate content.

A 15.1 g sample of the crude sucralose pentaacetate was dissolved in 100 ml of toluene at 80° C., and the solution thus produced filtered, cooled, and seeded. After filtration and vacuum drying the purified product was found to weight 13.1 g. A small sample was deacetylated as described above in Example 2 to provide a product consisting of 97.8 wt % sucralose, 1.8 wt % other chlorinated sucrose derivatives, and 0.4 wt % sucralose-6-acetate.

The once-purified sucralose pentaacetate was crystallized a second time from 100 ml of toluene (10.9 g recovery). A small sample was deacetylated as described above to give a product consisting of (basis total carbohydrate content) 99.2 wt % sucralose, 0.5 wt % other chlorinated sucrose derivatives, and 0.3% sucralose-6-acetate.

EXAMPLE 4

Acetylation of crude 6-O-benzoyloxy-4,1',6'-trichlorogalactosucrose

Crude 6-O-benzoyloxy-4,1',6'-tricholorogalactosucrose (10.1 g, 84.0% chrom. purity) was dissolved in a mixture of ethyl acetate (100 mL) and pyridine (10 mL) in a 3-neck 250-mL round bottom flask equipped with a thermometer, nitrogen purge and a drying tube. The solution was stirred (magnetic), cooled to 0° C. with an ice bath, acetic anhydride (10 mL) was added in a single portion, and the solution was allowed to warm to ambient temperature. The progress of the reaction was monitored by T.L.C. (toluene/ethyl acetate, 1:1). The reaction was not complete after about 2 hrs., so an additional 5 mL acetic anhydride was added to the solution and the reaction allowed to continue at ambient temperature overnight (T.L.C. single spot, Rf 0.65–0.67).

Water (50 mL) was added to the mixture to destroy unreacted anhydride, the solution was extracted with two 25 mL portions of 1N HCl, two 25-mL portions of saturated aqueous bicarbonate, and once with water. The organic layer was evaporated to a thick syrup (14.7 g) which was soluble in toluene and methanol, and sparingly soluble in aqueous methanol. A portion of this material was crystallized from a saturated solution in aqueous methanol.

What is claimed is:

1. A process for producing substantially pure sucralose pentaester from a mixture of 6-O-acyl-4,1',6'-trichloro-4,1',6'-trideoxygalactosucrose in a reaction medium comprising a tertiary amide, wherein said process comprises the steps of:
   (a) recovering the 6-O-acyl-4,1',6'-trichloro-4,1',6'-trideoxygalactosucrose from said mixture;
   (b) peracylating the 6-O-acyl-4,1',6'-trichloro-4,1',6'-trideoxygalactosucrose product of step (a) to produce thereby 4,1',6'-trichloro-4,1',6'-trideoxygalactosucrose pentaester; and
   (c) crystallizing the 4,1',6'-trichloro-4,1',640-trideoxygalactosucrose pentaester product of step (b) from a mixture of water and a substantially water-immiscible solvent to produce substantially pure 4,1',6'-trichloro-4,1',6'-trideoxygalactosucrose pentaester.

2. The process of claim 1 including the additional step of de-acylating the 4,1',6'-trichloro-4,1',6'-trideoxygalactosucrose pentaester to produce 4,1',6'-trichloro-4,1',6'-trideoxygalactosucrose.

3. The process of claim 1 wherein the tertiary amide reaction medium is N,N-dimethylformamide.

4. The process of claim 2 wherein the tertiary amide reaction medium is N,N-dimethylformamide.

5. The process of claim 1 wherein step (a) includes the step of removing the tertiary amide reaction medium by seam distillation.

6. The process of claim 2 wherein step (a) includes the step of removing the tertiary amide reaction medium by steam distillation.

7. The process of claim 3 wherein step (a) includes the step of removing the tertiary amide reaction medium by steam distillation.

8. The process of claim 4 wherein step (a) includes the step of removing the tertiary amide reaction medium by steam distillation.

9. The process of claim 5 wherein step (a) includes the step of an organic solvent extraction of the 6-O-acyl-4,1',6'-trichloro-4,1',6'-tridexoygalactosucrose following the removal of the tertiary amide reaction medium.

10. The process of claim 6 wherein step (a) includes the step of an organic solvent extraction of the 6-O-acyl-4,1',6'-trichloro-4,1,',6'-trideoxygalactosucrose following the removal of the tertiary amide reaction medium.

11. The process of claim 7 wherein step (a) includes the step of an organic solvent extraction of the 6-O-acyl-4,1',6'-trichloro-4,1',6'-trideoxygalactosucrose following the removal of the tertiary amide reaction medium.

12. The process of claim 8 wherein step (a) includes the step of an organic solvent extraction of the 6-O-acyl-4,1',6'-trichloro-4,1',6'-trideoxygalactosurose following the removal of the tertiary amide reaction medium.

13. The process of claim 9 wherein the organic solvent employed for the extraction is ethyl acetate.

14. The process of claim 10 wherein the organic solvent employed for the extraction is ethyl acetate.

15. The process of claim 11 wherein the organic solvent employed for the extraction is ethyl acetate.

16. The process of claim 12 wherein the organic solvent employed for the extraction is ethyl acetate.

17. The process of any one of claims 1-16 wherein the 6-O-acyl-4,1',6'-trichloro-4,1',6'-trideoxygalactosucrose is 6-O-acetyl-4,1',6'-trichloro-4,1',6'-trideoxygalactosucrose or 6-O-benzoyl-4,1',6'-trichloro-4,1',6'-trideoxygalactosucrose.

* * * * *